United States Patent [19]

Magó nee Karácsony et al.

[11] 4,108,855
[45] Aug. 22, 1978

[54] COMPOUNDS OF ERGOLENE AND ERGOLINE STRUCTURE AND METHOD FOR THE PREPARATION THEREOF

[75] Inventors: Erzsébet Magó nee Karácsony; Sándor Bajusz; József Borsi; Ildikó Kiraly; Endre Csányi; Istvan Polgári, all of Budapest, Hungary

[73] Assignee: Richter Gedeon Vegyeszeti Gyar Rt., Budapest, Hungary

[21] Appl. No.: 773,792

[22] Filed: Mar. 2, 1977

[30] Foreign Application Priority Data

Mar. 9, 1976 [HU] Hungary ............... GO 1332

[51] Int. Cl.² ........................... C07D 457/02
[52] U.S. Cl. ................. 260/285.5; 260/112.5 R; 424/274
[58] Field of Search ............ 260/285.5; 424/261

[56] References Cited

U.S. PATENT DOCUMENTS 4,005,089  1/1977  Mago et al. ............... 260/285.5

Primary Examiner—Donald G. Daus
Assistant Examiner—M. Vaughn
Attorney, Agent, or Firm—Young & Thompson

[57] ABSTRACT

The invention relates to a novel compound of the formula

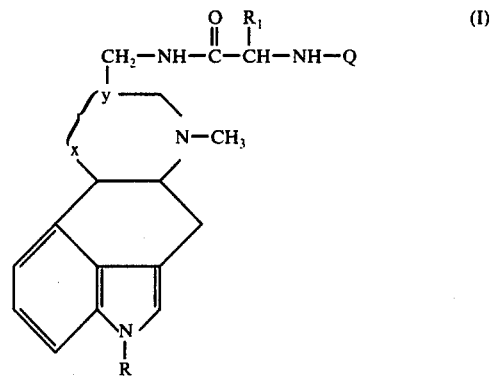

and the pharmaceuticlly acceptable acid addition salts thereof, wherein R stands for a hydrogen atom or methyl group, $x\ y$ designates a

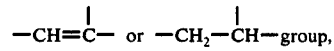

Q is a hydrogen atom or a benzyloxycarbonyl- or N-tert.-butyloxycarbonyl protective group, and $R_1$ is the side chain of a natural α-amino acid selected from the group consisting of Arg—, Tryp-13 , Phe—, Ser—, Leu—, Val—, Meth—, Tyr—, His— or Prol—-sidechain.

The compounds according to the invention possess antiserotonin and hypotensive effects and act upon the central nervous system.

10 Claims, No Drawings

COMPOUNDS OF ERGOLENE AND ERGOLINE STRUCTURE AND METHOD FOR THE PREPARATION THEREOF

The invention relates to novel compounds of ergolene and ergoline structure having the formula

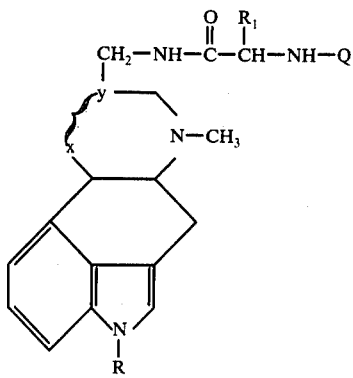

and to the pharmaceutically acceptable acid addition salts thereof. In formula I R represents a hydrogen atom or a methyl group, $xy$ a

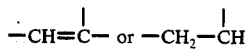

group, Q stands for a hydrogen atom or a benzyloxycarbonyl- (=Z) or a N-tert.-butyloxycarbonyl- (=Boz) protective group, and $R_1$ is the side chain of a natural α-amino acid selected from the group consisting of Arg—, Tryp—, Phe—, Ser—, Leu—, Val—, Meth—, Tyr—, His— and Prol— side-chain. Furthermore the invention relates to methods of preparation of said compounds.

Compounds with ergoline structure have fulfilled for many years an important role in therapy. They have an extremely broad action spectrum. TAKEO (Folia Pharmacol, Japan 58, 417 /1962/) observed the antiserotonin action of clavine alkaloids, mainly of elymoclavine in his in vitro and in vivo experiments. According to YUI and TAKEO (Japan J. Pharmacol. 14, 107 /1964/) the antiserotonin action of the 1-methyl derivatives of clavine alkaloids is several times higher than that of the starting compound.

Describing the results of recent pharmacological research FLOSS et al. (J. Pharm. Sci. 62, 699 /1973/), CASSADY et al. (J. Med. Chem. 17, 300 /1974/) and GEORGE S. LI et al. (J. Med. Chem. 18, 892 /1975/) came to the conclusion that the clavine alkaloids are useful gonadotropin inhibitors. As such they inhibit milk secretion and are specific prolactin inhibitors.

The object of the invention is to provide biologically active new ergolene and ergoline derivatives from 6-methyl-8-aminomethyl-Δ⁸-ergolene and -ergoline.

The invention is based on the discovery that this aim can be attained by reacting amino acids of the formula or their reactive derivatives

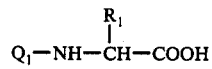

with amines of the formula

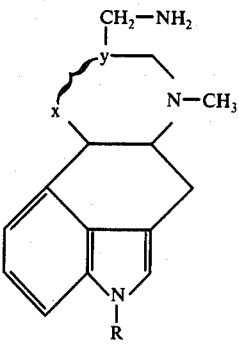

wherein $xy$, R and $R_1$ have the same meaning as above and $Q_1$ stands for a protective group used in the synthesis of peptides, or a reactive derivative of said amino acid.

The compounds of ergolene and ergoline structure of formula I and the acid addition salts thereof, wherein R represents a hydrogen atom or methyl group, $xy$ stands for a

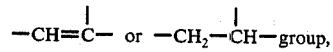

Q designates a hydrogen atom or a benzyloxycarbonyl- or N-tert. butyloxycarbonyl protective group, and $R_1$ stands for the side chain of a natural alpha-amino acid selected from the group consisting of the Arg—, Tryp—, Phe—, Ser—, Leu—, Val—, Meth—, Tyr—, His— or Prol— side-chain, can be prepared by reacting an amino acid of formula III the alpha-amino group of which being protected with $Q_1$, wherein the meaning of $Q_1$ is the same as above, or a reactive derivative of said amino acid with an amine of formula II, wherein $xy$ and R have the same meaning as above, and, if desired, the obtained product is N-methylated and/or hydrogenated and, if desired, the protective group is removed in a manner known per se. The product can be transformed into a pharmaceutically acceptable acid addition salt by treatment with an acid.

Acid anhydrides, acid azides, acid chlorides or active esters can be employed as reactive derivatives of the amino acids of formula III.

An advantageous method of implementation of the process according to the invention consists in dissolving an amino acid of formula III in dimethyl formamide, then forming a mixed anhydride with the iso-butyl ester of chloroformic acid in the presence of N-methyl morphine, and reacting said mixed anhydride with a solution of an amine of formula II in dimethyl formamide.

According to another preferred method of the invention an amino acid of formula III is dissolved in pyridine and an amine of formula II is added to said solution, using dicyclohexyl carbodiimide for the removal of water.

According to another advantageous method of preparation the hydrazide of an amino acid of formula II is prepared, then the azide is formed with sodium nitrite in an aqueous dioxane-hydrochloric acid medium, and said azide is reacted with an amine of formula II.

One can further proceed by suspending an amino acid of formula III in a mixture of methylene chloride and acetonitrile and reacting the obtained suspension for instance with pentachlorophenol in the presence of dicyclohexyl-carbodiimide and then reacting the obtained pentachlorophenyl ester with an amine of formula II.

If desired, the hydrogenation of the $\Delta^8$ double bond can be performed according to U.S. Pat. No. 3,029,943 in glacial acetic acid, in the presence of a platinum catalyst at a pressure of 3 atm. or according to YAMATODANI's method (Annual Report of the Research Takeda Laboratories 19, 1-24 /1960/) in ethanol, in the presence of Raney-Ni catalyst at a pressure of 65 atm. and at 65° C.

If desired, N-methylation can be performed with an alkyl halogenide in an alkali metal amide-ammonia system (TROXLER and HOFFMANN, Helv. Chim. Acta 40, 1721 /1957/; British patent specification No. 988,001).

The removal of the protecting group can be performed in a known way, for instance by means of catalytic hydrogenation (GROSSMANN, W., Berichte 91, 449 /1958/) or by means of treatment with an acid (D. ISHAI, J. Org. Chem. 17, 1564 /1952/).

The amine of formula II used as starting substance can be prepared from elymoclavine by reacting it with a tosyl or mesyl halogenide, preferably chloride, in ketone, preferably acetonitrile, in the presence of an acid-binding agent, preferably dicyclohexylamine, and the thus-obtained sulfonic acid ester is reacted with anhydrous ammonia and, if desired, the thus-obtained compound is N-methylated and/or the $\Delta^8$ double bond is hydrogenated.

The amino acids of formula III used also as starting materials can be prepared e.g. according to the methods described by GUTTMANN and BOISSONAS (Helv. Chim. Acta 41, 1852 /1958/, GREENSTEIN (Chemistry of the Amino Acids 2, 991 /1961/) and ERLANGER (J. Am. Soc. 73, 3508 /1951/).

The compounds of formula I act upon the central nervous system and have an antiserotonin and hypotensive action. Of the compounds with a neurodepressive effect the 6-methyl-8β-(N-benzyloxycarbonyl-L-arginyl)-amidomethyl-ergoline hydrochloride has a particularly typical neuroleptic action. This is manifest in the inhibited spontaneous motor activity of experimental animals after the administration of doses of 3 to 10 mg. of the said compound per kg. of body weight and in the inhibition of the psychostimulant action of amphetamine and of the emetic action of apomorphine. Said compound possesses in addition a narcosis-potentiating, a mild hypotensive and an antiserotonin action too.

It is characteristic of the antidepressant-type compounds that they antagonize by 1 to 30 mg. per kg. of body weight doses administered intraperitoneally or perorally the depressant and body-temperature-reducing effect of reserpine. 1,6-Dimethyl-8β-(N-benzyloxycarbonyl-L-seryl)amidomethyl-ergoline hydrochloride is, for instance, a compound of such antidepressant character.

The compounds of formula I can be transformed into pharmaceutical preparations in a known way, by admixing with pharmaceutically neutral additives, diluents and/or auxiliary agents.

The following Examples shall serve to further illustrate the invention, without, however, limiting the scope claimed.

EXAMPLE 1

6-Methyl-8-(N-benzyloxycarbonyl-L-arginyl)-amidomethyl-$\Delta^8$-ergolene hydrochloride 3.08 g. of N-benzyloxycarbonyl-L-arginine are dissolved under constant stirring in 100 ml. of dimethyl formamide. The solution is cooled to $-15°$ C and 1.39 ml. of the isobutyl ester of chloroformic acid and 1.1 ml. of N-methyl morpholine are added. After 5 minutes of stirring the solution of 2.55 g. of 6-methyl-8-aminomethyl-$\Delta^8$-ergolene in 20 ml. of dimethyl formamide is added. The reaction mixture is warmed slowly to room temperature, stirred at this temperature for 2 hours and then evaporated in vacuo. The residue is dissolved in a mixture of 100 ml. of isopropanol and 400 ml. of chloroform, and then 150 ml. of water are added. The pH of the solution is adjusted to 8 by the addition of a 10% ammonium hydroxide solution, and after shaking the organic phase is separated and the aqueous phase is extracted with a 1 to 4 mixture of isopropanol and chloroform. The organic phases are combined and dried over sodium sulphate and evaporated. Any eventual impurity is removed chromatographically on a column of 60 g. of silica gel. Elution is performed with a 30:0.3:9 mixture of chloroform:water:methanol. Column chromatography is followed by means of thin-layer chromatography. From the evaporation residue of the fractions salt is formed with hydrochloric acid in alcohol. The obtained 3.7 g. (61%) of 6-methyl-8-(N-benzyloxycarbonyl-L-arginyl)amidomethyl-$\Delta^8$-ergolene hydrochloride melts at 118 to 120° C. $(\alpha)_D^{20} = -58.1°$ (c = 0.5; 50% aqueous ethanol).

EXAMPLE 2

6-Methyl-8β-(N-benzyloxycarboyl-L-arginyl)-amidomethyl-ergoline hydrochloride

The title compound is prepared by means of the method described in Example 1 from 3.08 g. of N-benzyloxycarbonyl-L-arginine and 2.57 g. of 6-methyl-8β-aminomethyl-ergoline. The thus-obtained 4.16 g. (72%) of 6-methyl-8β-(N-benzyloxycarbonyl-L-arginyl)-aminomethyl-ergoline hydrochloride melts at 172° to 174° C. $(\alpha)_D^{20} = -21.75°$ (c = 0.5; 50% aqueous ethanol).

EXAMPLE 3

1,6-Dimethyl-8β-(N-benzyloxycarbonyl-L-seryl)-amidomethyl-ergoline hydrochloride 6 g. of N-benzyoxycarbonyl-L-serine-pentachlorophenyl ester are dissolved in a mixture of 200 ml. of anhydrous acetonitrile and 50 ml. of dimethyl formamide, the a solution of 2.69 g. of 1,6-dimethyl-8β-aminomethylergoline in 25 ml. of dimethyl formamide is added. Stirring is continued for 2 hours whereafter the mixture is evaporated. The residue is purified by column chromatography on a 60 g. silica gel column. Elution is performed with a 30:0.5:7.5 mixture of chloroform:water:ethanol. Column chromatography is followed by means of thin-layer chromatography. From the evaporation residue of the fractions salt is formed with hydrochloric acid in alcohol. Salt formation is promoted by the addition of ether. The obtained 3.4 g. (65%) of 1,6-dimethyl-8β-(N-benzyloxycarbonyl-L-seryl)-amidomethyl-ergoline melts at 110 to 111° C $(\alpha)_D^{20} = -39.7°$ (c = 0.5; 50% aqueous ethanol).

EXAMPLE 4

6-Methyl-8-(N-benzyloxycarbonyl-L-tyrosyl)-amidomethyl-Δ⁸-ergolene bimaleate 3.15 g. of N-benzyloxycarbonyl-L-tyrosine hydrochloride are suspended in 100 ml. of 0.1 N hydrochloric acid, 10 ml. of aqueous sodium nitrite solution and next 15 ml. of 1 N hydrochloric acid are added at 0° to 5° C to the suspension. Stirring is continued at this temperaturre for 15 minutes, then the reaction mixture is neutralized by the addition of a sodium hydrogen carbonate solution, and the amide formed in this way is extracted from the reaction mixture in three portions with a total of 2 litres of ether. The united ether fractions are dried with anhydrous potassium carbonate, filtered and the solution of 2.53 g. of 6-methyl-8-aminomethyl-Δ⁸-ergolene in 10 ml. of dioxane is added under stirring. Stirring is continued at room temperature for 4 hours. The reaction mixture is shaken with 250 ml. of water and the organic phase is separated. The aqueous phase is extracted twice with chloroform, the combined organic phases are dried over potassium carbonate and evaporated to dryness in vacuo. The residue is purified by means of column chromatography on a 60 g. silica gel column. Elution is performed with a 30:0.5:7.5 mixture of chloroform:water: :ethanol. Column chromatography is followed by means of thin-layer chromatography. From the evaporation residue of the fractions a salt is formed with maleic acid in alcohol. The obtained 4.65 g. (74%) of 6-methyl-8-(N-benzyloxycarbonyl-L-tyrosyl)-amidomethyl-Δ⁸-ergolene bimaleate melts at 164° to 168° C. $(\alpha)_D^{20} = -58.8°$ (c = 0.5; 50% aqueous ethanol).

EXAMPLE 5

6-Methyl-8β-(N-benzyloxycarbonyl-L-methionyl)-amidomethyl-ergoline

The title compound is prepared from 2.55 g. of 6-methyl-8β-aminomethyl-ergoline and 5.45 g. of N-benzyloxycarbonyl-L-methionyl-pentachlorophenyl ester by the method described in Example 3. The obtained 3.9 g. (76%) of 6-methyl-8β-(N-benzyloxycarbonyl-L-methionyl)-amidomethyl-ergoline melts at 134° to 136° C. $(\alpha)_D^{20} = -48.1°$ (c = 0.5; pyridine).

EXAMPLE 6

6-Methyl-8β-(N-benzyloxycarbonyl-L-phenylalanyl-)amidomethyl-ergoline

The title compound is prepared from 2.55 g. of 6-methyl-8β-aminomethyl-ergoline and 2.99 g. of N-benzyloxycarbonyl-L-phenylalanine with the method described in Example 1. The obtained 4.25 g. (71%) of 6-methyl-8β-(N-benzyloxycarbonyl-L-phenylalanyl)-amidomethyl-ergoline melts at 205° to 206° C. $(\alpha)_D^{20} = -58.0°$ (c = 0.5, pyridine).

EXAMPLE 7

1,6-Dimethyl-8β-(N-benzyloxycarbonyl-L-tryptophyl)-amidomethyl-ergoline

The title compound is prepared from 3.38 g. of N-benzyloxycarbonyl-L-trytophane and 2.55 g. of 1,6-dimethyl-8β-aminomethyl-ergoline by the aid of the method described in Example 1. The obtained 4.42 g. (75%) of 1,6-dimethyl-8β-(N-benzyloxycarbonyl-L-tryptophyl)-amidomethyl-ergoline melts at 133° to 135° C. $(\alpha)_D^{20} = -36.9°$ (c = 0.5; pyridine).

EXAMPLE 8

6-Methyl-8-(N-benzyloxycarbonyl-L-seryl)-amidomethyl-Δ⁸-ergolene hydrochloride The title compound is prepared from 2.53 g. of 6-methyl-8-aminomethyl-Δ⁸-ergolene and 6 g. of N-benzyloxycarbonyl-L-serine-pentachlorophenyl ester by way of the method described in Example 3. The obtained 3.57 g. (70%) of 6-methyl-8-(N-benzyloxycarbonyl-L-seryl)-amidomethyl-Δ⁸-ergolene hydrochloride melts at 123° C. $(\alpha)_D^{20} = -43°$ (base) (c = 0.5; pyridine).

What we claim is:

1. A compound of the formula

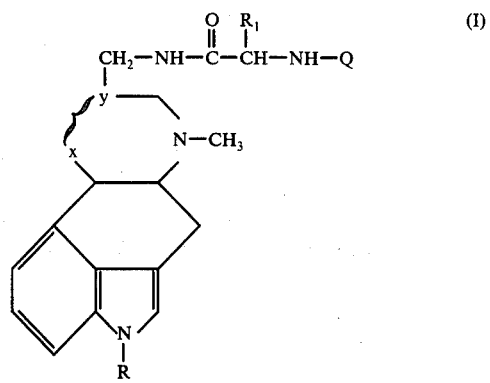

wherein R stands for a hydrogen atom or a methyl group, $\overline{x\,y}$ stands for a

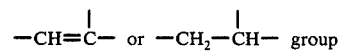

and Q designates a hydrogen atom or a benzyloxycarbonyl- or N-tert.-butyloxycarbonyl protective group, and R₁ represents the side-chain of a natural α-amino acid selected from the group consisting of Arg—, Tryp—, Phe—, Ser—, Leu—, Val—, Meth—, Tyr—, His— and Prol— side-chain, and the pharmaceutically acceptable acid addition salts thereof.

2. The compound as claimed in claim 1, being 6-methyl-8-(N-benzyloxycarbonyl-L-arginyl)-amidomethyl-Δ⁸-ergolene.

3. The compound as claimed in claim 1, being 6-methyl-8β-(N-benzyloxycarbonyl-L-arginyl)-amidomethyl-ergoline.

4. The compound as claimed in claim 1, being 1,6-dimethyl-8β-(N-benzyloxycarbonyl-L-seryl)-amidomethylergoline.

5. The compound as claimed in claim 1, being 6-methyl-8-(N-benzyloxycarbonyl-L-tyrosyl)-amidomethyl-Δ⁸-ergolene.

6. The compound as claimed in claim 1, being 6-methyl-8β-(N-benzyloxycarbonyl-L-methionyl)-amidomethyl-ergoline.

7. The compound as claimed in claim 1, being 6-methyl-8β-(N-benzyloxycarbonyl-L-phenylalanyl)-amidomethylergoline.

8. The compound as claimed in claim 1, being 1,6-dimethyl-8β-(N-benzyloxycarbonyl-L-tryptophyl)-amidomethylergoline.

9. The compound as claimed in claim 1, being 6-methyl8-(N-benzyloxycarbonyl-L-seryl)-amidomethyl-Δ⁸-ergolene hydrochoride.

10. A process for preparing a compound of formula I according to claim 1, wherein R stands for a hydrogen atom or a methyl group, $\widetilde{x\,y}$ stands for a

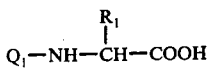

and Q designates a hydrogen atom or a benzyloxycarbonyl- or N-tert.-butyloxycarbonyl protective group, and R₁ represents the side-chain of a natural α-amino acid selected from the group consisting of Leu—, Val—, Meth—, Tyr—, His— and Prol— side-chain, characterized in that an amino acid of the formula $$Q_1-NH-\underset{\underset{R_1}{|}}{CH}-COOH \qquad (III)$$

wherein R₁ has the same meaning as above and Q₁ stands for a benzyloxycarbonyl or N-tert.-butyloxycarbonyl protective group, or a reactive derivative of said amino acid selected from acid anhydride, acid azide, acid chloride and active ester, is reacted with an amine of the formula

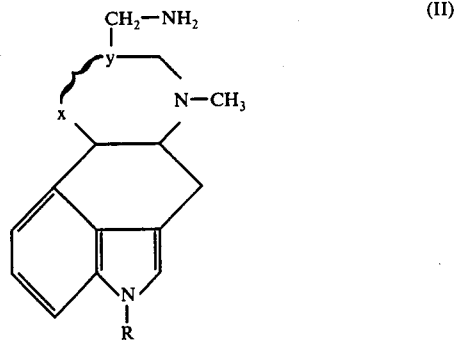

wherein R stands for a hydrogen atom or a methyl group and $\widetilde{x\,y}$ designates a

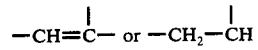

group.

* * * * *